US006380438B1

(12) United States Patent
Winter

(10) Patent No.: US 6,380,438 B1
(45) Date of Patent: Apr. 30, 2002

(54) PROCESS FOR THE PRODUCTION OF 3-HYDROXYPROPANAL

(75) Inventor: George Robert Winter, Fond du Lac, WI (US)

(73) Assignee: TTC Labs, Inc., Fond du Lac, WI (US)

( * ) Notice: Subject to any disclaimer, the term of this patent is extended or adjusted under 35 U.S.C. 154(b) by 0 days.

(21) Appl. No.: 09/615,941

(22) Filed: Jul. 13, 2000

(51) Int. Cl.⁷ ............................................. C07C 45/45
(52) U.S. Cl. ..................... 568/464; 568/463; 568/491; 568/861
(58) Field of Search ................................ 568/449, 459, 568/463, 464, 861, 491

(56) References Cited

U.S. PATENT DOCUMENTS

| | | |
|---|---|---|
| 2,434,110 A | 1/1948 | Hatch et al. |
| 2,639,295 A | 5/1953 | Hagemeyer |
| 3,536,763 A | 10/1970 | Eleuterio et al. |
| 4,408,079 A | 10/1983 | Merger et al. |
| 4,943,663 A | 7/1990 | Diekhaus et al. |
| 5,015,789 A | 5/1991 | Arntz et al. |
| 5,093,537 A | 3/1992 | Unruh et al. |
| 5,210,318 A | 5/1993 | Briggs et al. |
| 5,334,778 A | 8/1994 | Haas et al. |
| 5,364,984 A | 11/1994 | Arntz et al. |
| 5,576,471 A | 11/1996 | Semple et al. |
| 5,770,776 A | 6/1998 | Powell et al. |
| 5,821,092 A | 10/1998 | Nagarajan et al. |

OTHER PUBLICATIONS

Palion et al, React.Kinet.Catal.Lett., 1(4), 461–5, (1974). (Abstract only).*
D. Radlein, et al. "An Improved Upgrading Process for Heavy Oils and Bitumens", 47$^{th}$ Canadian Chemical Engineering Conference, Paper 135 (1 page), (1997).
"Zeolites", CASELECTS, vol. 1999, Issue 03, Feb. 8, 1999, pp. 1, 17, 18.
"Physics/Electronics", University of Delaware Technologies, 2 pages, Aug. 1983.
OptiCracking®: "Hydrocracking for the 21$^{st}$ Century", Process Associates, 1996, 2 pages.
B. Gunzel et al, Fermentative Production of 1,3–propanediol from Glycerol by Clostridium Butyricum up to a Scale of 2m³, Applied Microbiology and Biotecnology, vol. 36, No. 3, 1991, pp. 289–294.

* cited by examiner

Primary Examiner—Sreeni Padmanabhan
(74) Attorney, Agent, or Firm—Kenyon & Kenyon

(57) ABSTRACT

A process for producing 3-hydroxypropanal includes reacting formaldehyde and acetaldehyde to form an aqueous solution of acrolein; and hydrating the aqueous solution of acrolein to form 3-hydroxypropanal, wherein the aqueous solution of acrolein is capable of being hydrated to 3-hydroxypropanal without having to remove excess formaldehyde or acetaldehyde.

22 Claims, 1 Drawing Sheet

PROCESS FOR THE PRODUCTION OF 3-HYDROXYPROPANAL

FIELD OF THE INVENTION

The present invention relates to a process for the production of 3-hydroxypropanal.

BACKGROUND OF THE INVENTION

The monomer 1,3-propanediol has increasing utility in many applications, such as in the production of polyester fibers and polyurethanes. For example, 1,3-propanediol is viewed as an important component in the production of polytrimethylene terephthalate, a polyester which is particularly useful in the application of carpet fibers.

In the production of 1,3-propanediol, 3-hydroxypropanal is often formed as an intermediate or co-product, and exemplary processes for the production of 1,3-propanediol include: i) fermentation of glycerol, ii) hydration of olefinic aldehydes, and iii) epoxide hydroformylation. However, each of these processes can exhibit significant disadvantages.

As described by B. Gunzel et al. in Applied Microbiology and Biotechnology (1991), pages 289–294, fermentation of glycerol by various microorganism results in either 1,3-propanediol directly or 3-hydroxypropanal which is catalytically hydrogenated to 1,3-propanediol. Recently, microorganisms were also bioengineered to convert carbohydrates or glycerol to 1,3-propanediol; see U.S. Pat. No. 5,821,092. A disadvantage of some fermentation processes, however, is a low space-time yield. Moreover, recovery of 1,3-propanediol from highly diluted fermentation solutions is energy intensive.

Regarding the second type of process, the hydration of olefinic aldehydes such as acrolein may be accomplished by employing strongly ionized acids, as described in U.S. Pat. No. 2,434,110. Additionally, U.S. Pat. No. 3,536,763 describes the hydration of acrolein in the presence of weakly acidic carboxylic acid cation exchange resins such as Amberlite IRC-84 (Rohm & Haas) and Rexyn RG-51(4) (Fisher Scientific Co.). According to U.S. Pat. No. 3,536,763, 20% aqueous acrolein solution is pumped through the resin bed yielding high conversion of acrolein to 3-hydroxypropanal. The resulting aqueous solution is then hydrogenated at 100° C. under 130 atmosphere hydrogen pressure to produce an aqueous solution of 1,3-propanediol.

U.S. Pat. No. 5,015,789 also describes the hydration of acrolein and particularly discloses two stage processes for the production of 1,3-propanediol by acid-catalyzed hydration of acrolein to 3-hydroxypropanal followed by catalytic hydrogenation. A cation exchanger resin having aminophosphonate groups resulting in 3-hydroxypropanal selectivities up to 85% at 40% acrolein conversion is also disclosed therein.

U.S. Pat. Nos. 5,364,984 and 5,334,778 describe the hydrogenation of 3-hydroxypropanal to 1,3-propanediol on $Pt/TiO_2$ catalysts and on commercial transition-metal doped Raney Ni or Pt/C catalysts, respectively. U.S. Pat. No. 5,093,537 further discloses a hydration catalyst based on an alumina-bound zeolite which exhibits 85–90% selectivities to 3-hydroxypropanal at 40–60% acrolein conversions, with 3-hydroxypropanal hydrogenated on a Mo-promoted Raney Ni catalyst.

Although some of the processes of the second type may be characterized as having a relatively high space-time yield, they are typically disadvantageously based on isolated acrolein which is a highly toxic, unstable compound that does not lend itself easily to shipping or high volume storage. Moreover, acrolein is often produced by air oxidation of propylene on a fixed bed catalyst at elevated temperatures. Consequently, the acrolein plant and also the 1,3-propanediol plant would preferably need to be either an integral part of an existing olefines manufacture unit or located in its immediate vicinity.

Regarding the third type of process, epoxide hydroformylation, ethylene oxide may be reacted with synthesis gas (CO and $H_2$) under 65 atmosphere pressure and at a temperature of 110° C. in the presence of a catalysts comprising an anionic phosphorus ligand-rhodium containing complex, according to U.S. Pat. No. 5,210,318. However, the reaction product contains a mixture of 1,3-propanediol and 3-hydroxypropanal. Recently, Shell Oil Company has developed a process for the production of 3-hydroxypropanal based on the cobalt-catalyzed hydroformylation of ethylene oxide, but in order to achieve suitable space-time yield the reaction is carried out under elevated pressure (50–150 atmosphere) and in the presence of hydroquinone as a promoter; see U.S. Pat. No. 5,576,471. Yet another disadvantage of some hydroformylation processes is that although ethylene oxide is less toxic and more transportable than acrolein, a dedicated high-pressure hydroformylation unit utilizing high pressure syngas is required.

Accordingly, there exists a need for a process for the production of 3-hydroxypropanal potentially useful in the production of 1,3-propanediol, which process improves upon or eliminates disadvantages associated with previously known techniques.

SUMMARY OF THE INVENTION

In accordance with the present invention, an efficient process for producing 3-hydroxypropanal useful in the production of 1,3-propanediol was determined.

According to one embodiment of the present invention, a process for producing 3-hydroxypropanal comprises reacting formaldehyde and acetaldehyde to form, in a liquid phase and in the presence of a secondary amine mineral salt, an aqueous solution of acrolein; and hydrating the aqueous solution of acrolein to form 3-hydroxypropanal, wherein the aqueous solution of acrolein is capable of being hydrated to 3-hydroxypropanal without having to remove excess formaldehyde or acetaldehyde.

According to another embodiment of the present invention, a process for producing 3-hydroxypropanal comprises reacting formaldehyde and acetaldehyde in a liquid phase catalytic reactor using a secondary amine mineral acid salt, either in a solution or immobilized on a fixed macroporous resin bed.

According to yet another embodiment of the present invention, the formaldehyde and acetaldehyde are fed to an immobilized secondary amine salt catalyst bed in an equimolar ratio and the reaction product is an aqueous solution substantially free of non-reacted materials.

An advantage of the present invention is that there is no need for a dedicated acrolein production plant, nor is there a need for storage or handling of free acrolein. As a result, a large capital investment in an acrolein production plant is avoided.

Another advantage of the present invention is avoiding the hazards and costs of handling large acrolein inventories.

Yet another advantage of the present invention is the useful application of commodities such as acetaldehyde and formaldehyde thereby avoiding the need to locate a production plant in a geographical vicinity of ethylene oxide, syngas or propylene facilities.

Other features and advantages of the present invention will be readily apparent in view of the following drawing and detailed description of the invention.

DETAILED DESCRIPTION OF THE INVENTION

Figure 1:
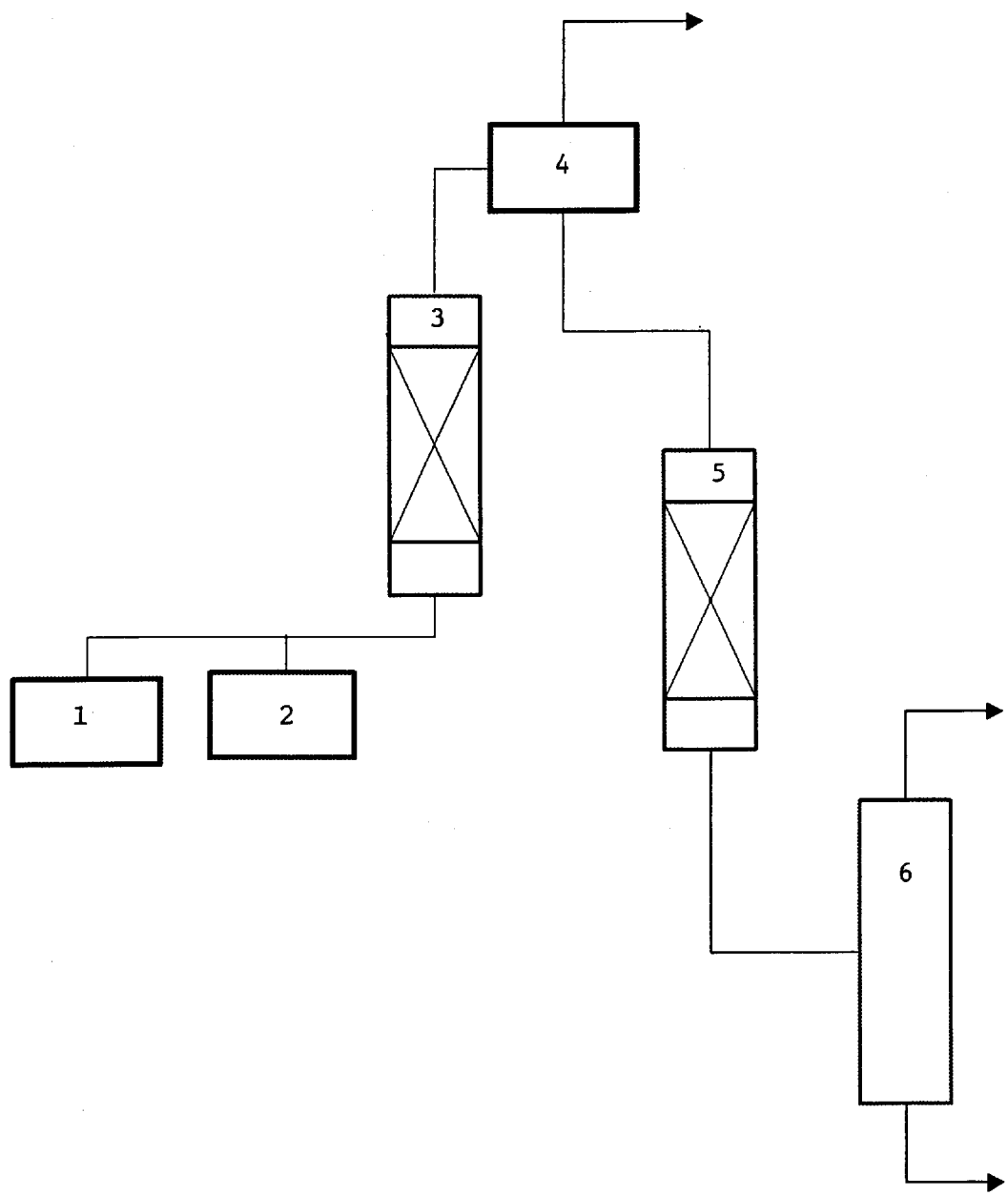
FIG. 1 illustrates an embodiment of the process of the present invention.

As a first step in the process according to the present invention, formaldehyde is reacted with acetaldehyde. The formaldehyde or formalin is preferably employed in aqueous form, such as between about 10 mole % and about 45 mole % aqueous solution and preferably between about 30 mole % and about 45 mole % aqueous solution. Most preferably, about 37 mole % is employed. The use of a solvent apart from water is not necessary. However, a polymerized form of formaldehyde such as trioxane may be employed. In this case, the use of a solvent apart from water in which the formaldehyde can be dissolved is beneficial and acceptable solvents include, but are not limited to, hydrocarbons and aliphatic alcohols, e.g. toluene, isodecane and 2-ethylhexanol.

The starting formaldehyde and acetaldehyde are preferably present in approximately equimolar amounts to produce a reaction product which is substantially free of non-reacted materials. Most preferably, equimolar amounts are employed. Accordingly, an excess amount of formaldehyde or acetaldehyde is not required for complete conversion to acrolein. However, it is also possible to use one of the constituents in excess of the other. For example, from about 1.5 to about 4 moles of acetaldehyde per mole of starting formaldehyde may be used, as well as from about 2 to about 3 moles of acetaldehyde per mole of starting formaldehyde. If an excess is used, the excess amount results in an unreacted amount of acetaldehyde which may be recovered by distillation from the acrolein aqueous solution.

The reaction of the present invention is advantageously carried out by contacting the afore-described solution of formaldehyde and acetaldehyde with a catalytically effective amount of a catalyst, such as a secondary amine salt either in a solution or immobilized on a fixed macroporous resin bed such as a polymeric resin made of highly cross linked styrene divinyl benzene. A low cross linked resin (gel type) readily known to those skilled in the art may also be used, however, it may have poor mechanical properties and disintegrate under high shear flow conditions.

The secondary amine salt in solution is present in an amount between about 1 and about 10 mole %, and preferably between about 2 and about 5 mole %. Exemplary secondary amine salts of carboxylic acids as catalysts are described in U.S. Pat. No. 4,943,663. For example, suitable catalysts include dialkyl hydrochlorides such as dimethyl, diethyl, diethanol, dipropyl, di-n-butyl, diisobutyl, diisoamyl and dibenzyl amine. Branched chain dialkyl amine hydrochlorides such as diisopropylamine or diisobutylamine are acceptable, but are less effective. Cyclic aliphatic amines such as piperidine, morpholine and piperazine are also suitable. Similarly, hydrobromides, sulphates, phosphates, etc. can also be used. The preferred catalysts, however, are the hydrochlorides of secondary acyclic amines, in particular bis (2 methoxy ethyl)-amine hydrochloride, di-n butylamine hydrochloride, di-benzylamine hydrochloride and n benzyl-n butylamine hydrochloride. Accordingly, we have found that aliphatic secondary amine salts of mineral acids, in particular bis 2 methoxy ethyl amine hydrochloride are most suitable catalysts.

In an alternative embodiment of the present invention, an immobilized amine hydrochloride catalyst may be employed in place of the soluble secondary amine hydrochloride. For example, primary amines such as benzylamine or 2 methoxy ethyl amine or 2-(2-methoxy ethyl amine)-ethanol, may be monoalkylated by reaction with chloromethylated macroporous highly cross-linked styrene-divinyl benzene copolymer resulting in a polymer containing secondary dialkyl amine hydrochloride groups. Such catalysts are well known in the art and commercially available. Using catalysts of this type in a trickle bed form (e.g. fixed bed) allows simple separation of the resulting aqueous acrolein solution from the fixed catalyst bed.

The reaction can be carried out at atmospheric pressure, reduced or even increased pressure, and preferably it is carried out at a pressure between about 1 kg/cm$^2$ g and about 5 kg/cm$^2$ g.

The pH of the reaction is neutral or preferably in the range of about 4 and about 6 to minimize secondary condensations.

Typically, the temperature of the reaction is in the range of about −5° C. and 120° C., preferably between about 20° C. and about 40° C., and the reaction contact of the constituents is preferably carried out by mixing the amine salt into the formaldehyde-acetaldehyde solution.

A tubular type reactor readily known to those skilled in the art is particularly advantageous for carrying out the process of the present invention. Use of such a reactor would advantageously include feeding the formaldehyde/acetaldehyde/amine salt aqueous solution into a tubular reactor designed to operate under high turbulence conditions which entail intimate mixing and favorable mass transfer conditions.

Alternatively, the aqueous formaldehyde/acetaldehyde/amine salt solution may be fed into a conventional tubular packed reactor (e.g. packed by commercial packing such as ceramic saddles or metal Intalox), thereby achieving an intimate contact on the surface of the inert packing. Such inert packing may increase the turbulence across the packing thereby facilitating contact between the reactants.

Upon reaction of the formaldehyde, acetaldehyde and amine salt, an aqueous solution of acrolein is produced which is then preferably immediately subjected to hydration. Advantageously, removal of excess unreacted formaldehyde or acetaldehyde prior to hydration is not required. Thus, a significant advantage of the process of the present invention is that it is not necessary to distill off any excess unreacted starting materials nor isolate the acrolein prior to hydration. This is a significant advantage and improvement over prior art processes.

In prior art processes acrolein would have to be isolated, purified, stored and handled separately, whereby in the process of this invention acrolein aqueous solution is reacted in situ and is subsequently converted to 3-hydroxypropanal. Thus, in the process of the present invention, the need to handle acrolein inventory is advantageously avoided.

The reaction may be advantageously, spontaneously induced by passing the mixture of aqueous formaldehyde, acetaldehyde and amine salt through a reactor heated to between about 50° C. and about 120° C., preferably between about 90° C. and about 110° C., at a rate which will effect full conversion of acrolein. For instance, a liquid hourly space velocity (LHSV) of about 0.05 LHSV to about 0.9 LHSV, preferably about 0.4 LHSV, may be employed. One skilled in the art would realize that the rate may be dependent upon factors such a type of reactor, volume, liquid feed distributor, reactor internals, reactor D/H, reaction conversion rate, etc.

To minimize acrolein polymerization, an inhibitor such as tertiary butyl catechol or dibutyl p-cresol may optionally be added in an amount of between about 0.05% mole and about 2% mole, preferably between about 0.1 mole % and about 1.5 mole %. Exemplary polymerization inhibitors are described in U.S. Pat. No. 3,536,763. For instance, the inhibitor may be added to the aqueous formaldehyde solution containing the acetaldehyde and the secondary amine hydrochloride.

The aqueous solution of acrolein may then be fed preferably at the rate of its formation, into a cation exchange resin column to effect full conversion of the acrolein to 3-hydroxypropanal. Thus, an advantageous feature of the present invention is that a one pot reactor may be employed. For example, the starting materials may be directly and fully converted to 3-hydroxypropanal with the use of only one reactor such that the generated acrolein is not isolated prior to conversion. Advantageously, full conversion may be reached in a single reactor.

One skilled in the art would however appreciate that multiple units may also be employed. For example, a system which consists of two tubular reactors in series, one for acrolein solution formation and the other for 3-hydroxypropanal formation, or alternatively a column reactor which contains two catalyst layers, may be employed.

The column into which the aqueous solution of acrolein enters is preferably packed with beads of a weakly acidic carboxylic cation exchange resin, such as IRC-84, available from Rohm & Haas and containing from 0.1 to 1% calcium ions, as described in U.S. Pat. No. 3,536,763. For instance, the hydration catalyst may be a cation exchanger including aminophosphonate groups.

However, other methods of hydrating acrolein to 3-hydroxypropanal readily known to those skilled in the art may also be employed.

Preferably, the cation exchange resin temperature is between about 80° C. to about 110° C., and the pressure during the production of 3-hydroxypropanal is between about 0.3 kg/cm$^2$ g and about 35 kg/cm$^2$ g. Preferred pressure is between about 1 kg/cm$^2$ g and about 4 kg/cm$^2$ g, and about 1.5 kg/cm$^2$ g to about 2 kg/cm$^2$ g is typically employed. The solution should be maintained in such conditions where acetaldehyde is in liquid form.

It is also advantageous to use a closed system to prevent volatilization losses from the reaction mixture of the low boiling components such as acetaldehyde and acrolein. The initial concentration of the formaldehyde and acetaldehyde should preferably be between about 15% and about 30% to ensure a rapid conversion rate.

When a secondary amine hydrochloride catalyst is used in an immobilized form, the column may be packed with beads of the immobilized secondary amine hydrochloride. The formaldehyde-acetaldehyde solution may then be fed as described above into the column maintained at a suitable temperature, such as between about −5° C. and about 120° C., preferably between about 20° C. and about 40° C. at a LHSV of about 0.05 to about 1.0, preferably about 0.4. The generated acrolein solution may then be concurrently hydrated on the fixed bed cation exchanger catalyst.

Beads of multiple catalyst types may be packed in a multi-layer arrangement (such as a two layer arrangement with the secondary amine catalyst on top) or in a mixed mode wherein the column is packed with a mixture of resin catalysts, one resin comprised of a secondary amine anion exchanger (immobilized secondary amine hydrochloride) and the second comprised of a weakly acidic cation exchanger (immobilized carboxylic acid salt).

During the process of the present invention, the concentration of produced acrolein is advantageously kept at a minimum by maintaining the appropriate controlled feed rate of reactants into the column. This is done by controlling the acrolein producing reactants in such a way that the rate of acrolein formation is about the rate by which the latter is converted to 3-hydroxypropanal. This may be accomplished by sampling and analyzing the reactor products and subsequently adjusting residence time/flow rate as required. The acrolein is rapidly hydrated by the catalyst employed, resulting in full conversion to the more stable 3-hydroxypropanal, thus minimizing undesirable polymerizations of acrolein and secondary condensations of acetaldehyde. The solution emerging from the column contains 3-hydroxypropanal which is not isolated but advantageously sent to the hydrogenation stage.

If desired, the aqueous hydroxypropanal solution emerging from the column may then be converted to 1,3-propanediol by conventional catalytic hydrogenation processes, such as those described in U.S. Pat. No. 5,770,776. After removal of the hydrogenation catalyst, the 1,3-propanediol may then be recovered by distillation. When a soluble secondary amine hydrochloride catalyst is used, the distillation residue containing the secondary amine hydrochloride catalyst may be recycled back into the process.

Commercial catalysts such as molybdenum promoted Raney nickel catalyst operating at about 20° C. to about 120° C. and at up to about 250 psi of hydrogen pressure result in essentially quantitative yield of 1,3-propanediol in less than about 1 hour, as described in U.S. Pat. No. 5,093,537. Other noble metal catalysts such as platinum on alumina or copper chromite, as described in U.S. Pat. No. 3,536,763, may also be used.

Referring now to the embodiment of the present invention as shown in FIG. 1, FIG. 1 illustrates a continuous operation mode for the production of 3-hydroxypropanal, starting from formaldehyde and acetaldehyde. In particular, an aqueous solution of formaldehyde from storage 1 and acetaldehyde from storage 2 are fed simultaneously with the use of metering pumps into reactor 3 which is packed with a fixed bed of immobilized catalyst. The reactor operates at about 110° C. and 2.5 kg/cm$^2$ g pressure, and the reactor effluent is fed to a stripper-stabilizer 4 for lights stripping/polishing. The stabilized aqueous solution product of acrolein is pumped to the 3-hydroxypropanal reactor 5 which is packed with an ion exchange resin where the aqueous acrolein solution is directly converted to 3-hydroxypropanal. The 3-hydroxypropanal reactor operates at about 95° C. and 2 kg/cm$^2$ g. Aqueous solution of 3-hydroxypropanal is then fed into water stripper 6, where water is stripped off thereby bringing the 3-hydroxypropanal solution to the required composition which is suitable for a next hydrogenation step, as desired.

The examples which follow describe the invention in detail with respect to showing how certain specific representative embodiments thereof can be made, the materials, apparatus and process steps being understood as examples that are intended to be illustrative only.

EXAMPLE 1

A glass reactor is charged with a solution of 37% aqueous formalin (160 g, 1.97 mol). The solution is stirred for about 15 minutes while being cooled to 5° C., followed by addition of acetaldehyde (87 g, 1.977 mol). The catalyst which consists of bis (2 methoxy ethyl) amine hydrochloride (32.5 g) is then added followed by 5.9 g of N-nitrosodiphenyl amine as a radical polymerization inhibitor.

A cation exchange resin IRC-748 (780 ml) which is an amino acetic acid cation exchange resin commercially available from Rohm & Haas is charged to another (stirred) reactor (3L) equipped with a dip-pipe terminated by a stainless steel fritted filter with an average pore diameter of 50–100 micron fritted filter. The beads are covered with a minimum amount of water (ca.1000 ml) and are then heated for one hour to 110° C. During the heating period, the beads are moderately stirred by an anchor type agitator.

The cold formaldehyde-acetaldehyde solution, including the admixed secondary amine salt and the polymerization inhibitor is added at a rate of 2 g/min to the top of the stirred reactor maintained at 92° C. with the aid of a metering pump. During the addition, the temperature of the reaction mixture rises to 98° C. and the pressure is 2.7 kg/cm$^2$ g.

After 2.5 hours, the addition is completed. Heating is continued for an additional 1.5 hrs to 105° C., and the contents of the reactor are then cooled to room temperature. The resulting aqueous solution contains 3-hydroxypropanal is forced out of the reactor through the fritted dip-pipe by applying a positive nitrogen pressure above the liquid surface. Analysis indicated that 80% of the formaldehyde was converted to give 18.0 g of 3-hydroxypropanal.

EXAMPLE 2

A 2.5×30 cm stainless steel column is packed with 145 ml beads of IRC-748 cation exchanger from Rohm & Haas. The beads are covered with water. The column is connected by ⅛ stainless steel pipe to a metering pump in one side, while the outlet of the column is connected by means of a stainless steel tubing to a closed 2L stainless steel receiver equipped with a pressure gage and cooled by internal coil containing circulated cooling water at 20° C. The packed column is immersed in an oil bath maintained at 107° C. by a temperature control device. An aqueous 37% formalin (125 g) containing acetaldehyde (67 g) 2.5 g butylated hydroxyanisole and bis (2 methoxy ethyl) amine hydrochloride (16 g) is fed to the column inlet at a rate of 1 g/min. When the addition was complete, it was found by analysis of the receiver content that 78% of the formaldehyde was reacted to give 86.5 g of 3-hydroxypropanal in water.

EXAMPLE 3

The reaction was performed as in example 2, except that the column was packed with a mixture of 60 ml IRC-748 beads and 85 ml beads of immobilized secondary amine hydrochloride. At the end of the experiment it was found that the receiver contains 84.5 g of 3-hydroxypropanal on 76% conversion rate based on formaldehyde.

The afore-described examples advantageously demonstrate the efficiency of producing acrolein in situ with simultaneous conversion to 3-hydroxypropanal.

Accordingly, a significant advantage of the process of the present invention is that a safer and direct acrolein synthesis route may be employed.

Yet another advantage of the present invention is that the acrolein intermediate inventory is minimized due to the fact that in situ acrolein conversion to 3-hydroxypropanal is implemented.

While specific embodiments and steps have been described above, it should be readily apparent to those who are skilled in the art that the above-described embodiments and steps are exemplary in nature because certain changes may be made thereto without departing from the teachings of the invention, and the exemplary embodiments should not be construed as limiting the scope of protection for the invention as set forth in the appended claims. Thus, it is to be understood and expected that variations in the principles of the invention herein disclosed may be made by one skilled in the art and it is intended that such modifications are to be included within the scope of the present invention.

Additionally, all publications and patents cited in this specification are herein incorporated by reference in their entireties as if each individual publication or patent were specifically and individually indicated to be incorporated by reference.

What is claimed:

1. A process for producing 3-hydroxypropanal comprising:
reacting formaldehyde and acetaldehyde in a liquid phase to form an aqueous solution of acrolein intermediate product using a catalyst followed by directly hydrating the resulting aqueous solution of acrolein intermediate product to form 3-hydroxypropanal without isolating or handling the acrolein intermediate product, wherein the aqueous solution of acrolein intermediate product is capable of being hydrated to 3-hydroxypropanal without having to remove excess formaldehyde or acetaldehyde.

2. The process of claim 1 comprising contacting the formaldehyde and acetaldehyde with a amine salt catalyst.

3. The process of the claim 1 comprising contacting the formaldehyde and acetaldehyde with a catalyst selected from the group consisting of aliphatic secondary amine salts of mineral acids, dialkyl hydrochlorides, hydrobromides, sulphates, phosphates, secondary alicyclic amines, bis 2 alkoxy alkyl amines, bis 2 methoxy ethyl amine hydrochloride, di-n butylamine hydrochloride, n benzyl-n butylamine hydrochloride, piperidine, morpholine and piperazine.

4. The process of claim 2 comprising contacting the formaldehyde and acetaldehyde with an amine salt between about 1 mole % and about 10 mole %.

5. The process of claim 4 comprising contacting the formaldehyde and acetaldehyde with an amine salt between about 2 mole % and about 5 mole %.

6. The process of claim 1 wherein the formaldehyde and acetaldehyde are reacted in equimolar amounts.

7. The process of claim 1 wherein the formaldehyde is in aqueous form, between about 10 mole % and about 45 mole %.

8. The process of claim 7 wherein the formaldehyde is in aqueous form, between about 30 mole % and 45 mole %.

9. The process of claim 1 wherein an immobilized amine hydrochloride catalyst is contacted with the formaldehyde and acetaldehyde.

10. The process of claim 2 comprising passing a mixture of formaldehyde, acetaldehyde and secondary amine salt through a reactor heated to between about 50° C. and about 120° C. to effect full conversion of acrolein.

11. The process of claim 10 wherein the reactor is heated to between about 90° C. and about 110° C.

12. The process of claim 1 comprising adding an inhibitor to minimize acrolein polymerization.

13. The process of claim 1 comprising passing the aqueous solution of acrolein into a column at about its rate of production to effect conversion of the acrolein to 3-hydroxypropanal.

14. The process of claim 1 wherein the aqueous solution of acrolein is fed to a hydration reactor comprising a fixed bed hydration catalyst.

15. The process of claim 14 wherein the hydration catalyst is an ion exchange resin.

16. The process of claim 14 wherein the hydration catalyst is a cation exchanger including aminophosphonate groups.

17. The process of claim 2 wherein the aqueous acrolein is converted to 3-hydroxypropanal instantaneously.

18. The process of claim 2 wherein the formaldehyde and acetaldehyde are reacted in a liquid phase catalytic reactor using a secondary amine mineral salt, in a solution or on a fixed ion exchange resin bed.

19. The process of claim 1 further comprising catalytically hydrogenating the 3-hydroxypropanal to 1,3-propanediol.

20. A process for producing 3-hydroxypropanal comprising:

in a liquid phase reacting formaldehyde, acetaldehyde and an amine salt to form an aqueous solution of acrolein intermediate product, followed by directly hydrating the aqueous solution of acrolein intermediate product to form 3-hydroxypropanal without isolating or handling the acrolein intermediate product.

21. A process for producing 3-hydroxypropanal comprising:

in a liquid phase reacting formaldehyde and acetaldehyde to form an aqueous solution of acrolein intermediate product, wherein an excess amount of formaldehyde and acetaldehyde is not required for complete conversion to the acrolein intermediate product, followed by directly hydrating the aqueous solution of acrolein intermediate product to form 3-hydroxypropanal without isolating or handling the acrolein intermediate product.

22. The process of claim 1 wherein the process is carried out in a single reactor.

* * * * *